US010888184B2

(12) United States Patent
Levin

(10) Patent No.: US 10,888,184 B2
(45) Date of Patent: *Jan. 12, 2021

(54) SYSTEMS, APPARATUSES, COMPUTER READABLE MEDIA, AND METHODS FOR IMPLEMENTING A WIRELESSLY-ENABLED LIQUID CONTAINER

(71) Applicant: Prodigy Technology, LLC, Sheridan, WY (US)

(72) Inventor: Laurie J. Levin, New York, NY (US)

(73) Assignee: Prodigy Technology, LLC, Sheridan, WY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/183,379

(22) Filed: Nov. 7, 2018

(65) Prior Publication Data

US 2020/0138211 A1     May 7, 2020

(51) Int. Cl.
| | | |
|---|---|---|
| *A47G 19/22* | (2006.01) | |
| *G06F 3/16* | (2006.01) | |
| *H04L 29/08* | (2006.01) | |
| *A61J 11/04* | (2006.01) | |
| *G09B 5/04* | (2006.01) | |
| *A61J 9/00* | (2006.01) | |
| *H04W 4/80* | (2018.01) | |

(52) U.S. Cl.
CPC ..... *A47G 19/2227* (2013.01); *A47G 19/2272* (2013.01); *A61J 9/00* (2013.01); *A61J 11/04* (2013.01); *G06F 3/16* (2013.01); *G09B 5/04* (2013.01); *H04L 67/26* (2013.01); *H04W 4/80* (2018.02); *A47G 2019/2244* (2013.01); *A61J 2200/70* (2013.01); *A61J 2205/70* (2013.01)

(58) Field of Classification Search
CPC ... A47G 19/2227; A74G 19/2272; A61J 9/00; A61J 11/04; G06F 3/16; G09B 5/04; H04L 67/26
USPC ........................................................ 340/541
See application file for complete search history.

(56) References Cited

U.S. PATENT DOCUMENTS

| | | | |
|---|---|---|---|
| 4,678,093 A * | 7/1987 | Allen ...................... | A61J 9/00 200/220 |
| 4,898,060 A * | 2/1990 | To ............................ | A61J 9/00 215/11.1 |
| 4,944,704 A | 7/1990 | Grace | |
| 5,489,893 A | 2/1996 | Jo et al. | |
| 5,662,406 A | 9/1997 | Mattice et al. | |
| 5,842,901 A * | 12/1998 | Montgomery ............ | A61J 9/00 446/77 |

(Continued)

OTHER PUBLICATIONS

International Search Report and Written Opinion issued by ISA/US in PCT/US2019/060222, dated Jan. 16, 2020.

*Primary Examiner* — Kerri L McNally

(74) *Attorney, Agent, or Firm* — Nixon & Vanderhye P.C.

(57) ABSTRACT

The present invention is directed to systems, apparatuses, computer readable media, and methods implementing a wirelessly-enabled liquid container that can be remotely and dynamically configured to facilitate use-based messaging for a particular consumer of the contents of the liquid container. By way of example, a wirelessly-enabled baby bottle is provided that can be dynamic configured to facilitate use-based educational messaging for a particular child consumer of the contents of the liquid container.

25 Claims, 6 Drawing Sheets

(56) References Cited

U.S. PATENT DOCUMENTS

| | | | | |
|---|---|---|---|---|
| 6,024,625 A | * | 2/2000 | Pearce | A61J 9/00 215/11.1 |
| 6,104,292 A | * | 8/2000 | Rombom | A61J 9/00 340/573.1 |
| 6,652,346 B1 | * | 11/2003 | Arnold, III | A61J 9/00 215/11.1 |
| 7,134,932 B1 | * | 11/2006 | Carrasco | A61J 9/00 446/227 |
| 7,607,629 B1 | * | 10/2009 | Carrasco | A61J 9/06 248/102 |
| 2015/0285775 A1 | | 10/2015 | Gurumohan et al. | |
| 2016/0025545 A1 | | 1/2016 | Saltzgiver et al. | |
| 2016/0159632 A1 | | 6/2016 | Wheatley et al. | |
| 2017/0013982 A1 | | 1/2017 | Amaru | |
| 2017/0263102 A1 | | 9/2017 | Tshilombo et al. | |
| 2017/0332845 A1 | | 11/2017 | Kramer | |
| 2017/0340146 A1 | | 11/2017 | Alexander | |
| 2018/0344576 A1 | * | 12/2018 | Somsen | A61J 9/0653 |
| 2019/0096224 A1 | * | 3/2019 | Shoham | A61J 11/00 |

* cited by examiner

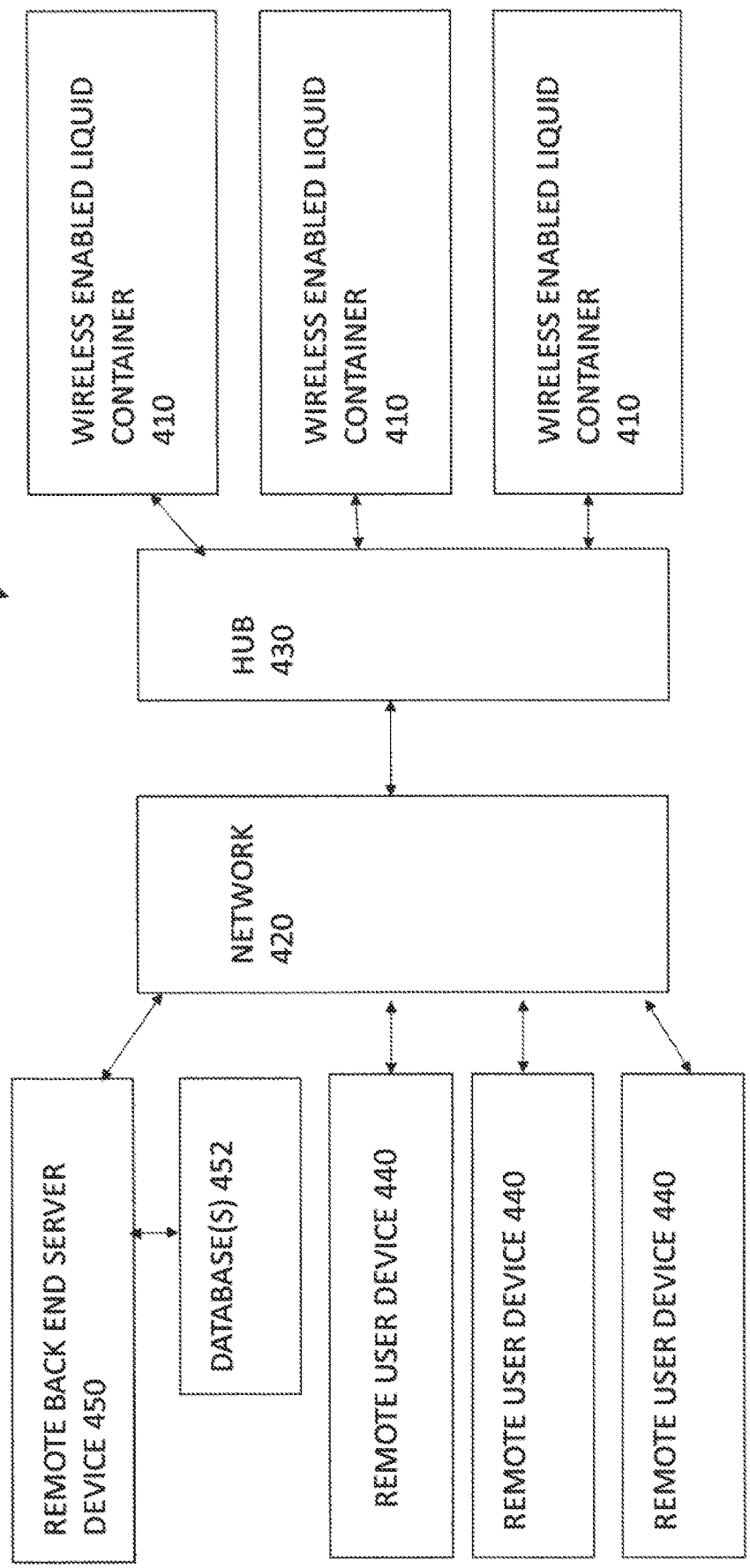

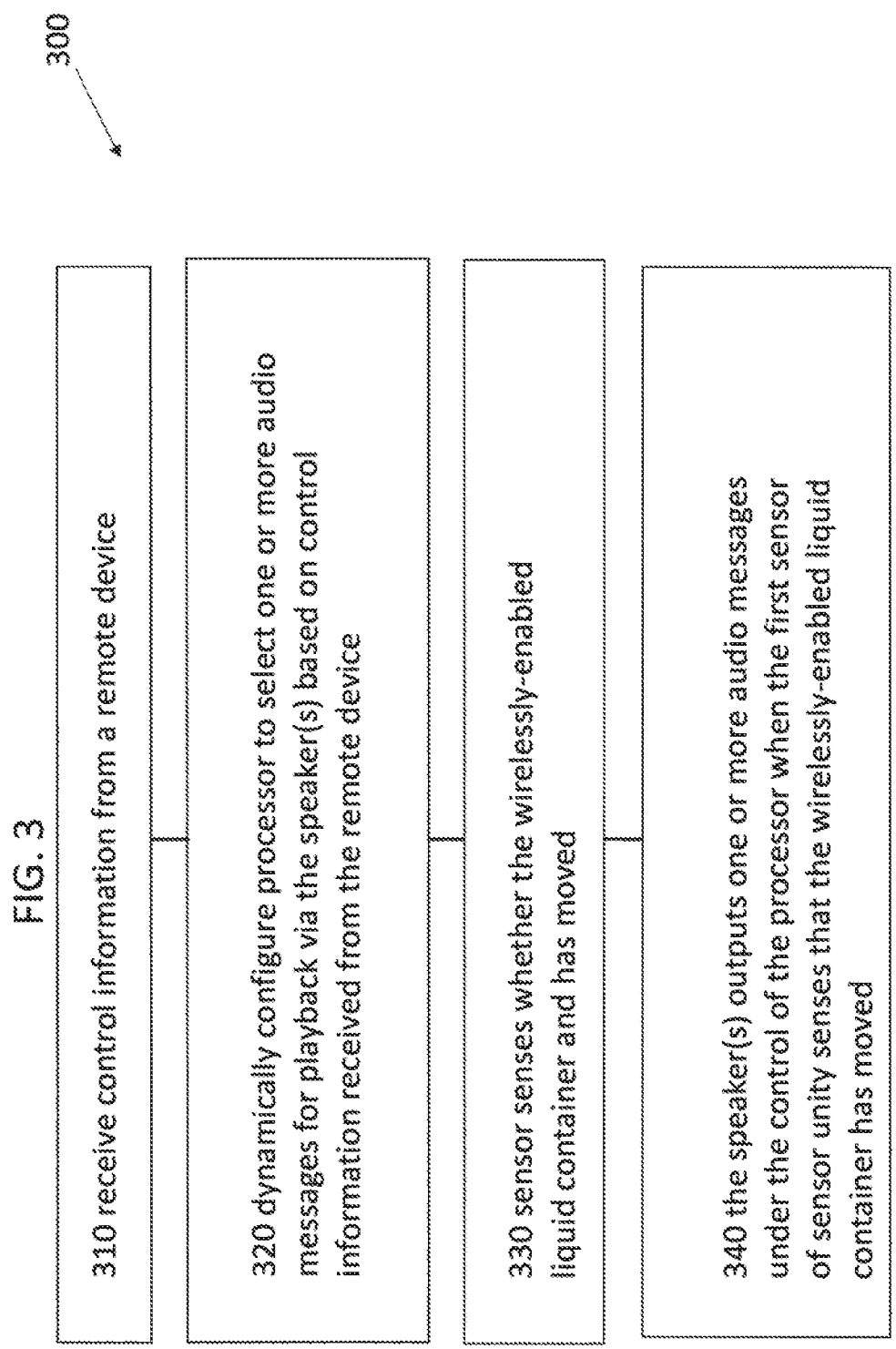

SYSTEMS, APPARATUSES, COMPUTER READABLE MEDIA, AND METHODS FOR IMPLEMENTING A WIRELESSLY-ENABLED LIQUID CONTAINER

TECHNICAL FIELD

The present invention is directed to systems, apparatuses, computer readable media, and methods for implementing a wirelessly-enabled liquid container that can be remotely and dynamically configured to facilitate use-based messaging for a particular consumer of the contents of the liquid container. It is particularly useful for implementing a wirelessly-enabled baby bottle or sippy cup that can be remotely and dynamically configured to facilitate, for example, use-based educational messaging for a particular child consumer of the contents of the liquid container.

BACKGROUND

Liquid containers provide an opportunity for use-based messaging while the liquid contents of those liquid containers are being consumed. By way of example, when the liquid contents of a baby bottle or sippy cup are being consumed by an infant or toddler, there is an opportunity to provide use-based messaging such as educational messaging to enhance a child's learning experience. Liquid containers have been described that include messaging capabilities, such as U.S. Pat. No. 7,134,932, which is directed to a musical baby bottle. However, these liquid containers have static capabilities, such that their messaging capabilities do not change once the liquid containers are deployed. What is needed is a wirelessly-enabled liquid container including a processor that can be remotely and dynamically configured to change the liquid container's messaging capabilities for a particular consumer, such as a child in the case of a baby bottle or sippy cup.

SUMMARY

In accordance with illustrative embodiments of the present invention, systems, apparatuses, computer readable media, and methods are provided for implementing a wirelessly-enabled liquid container that can be dynamically configured to facilitate use-based messaging for a particular consumer of the contents of the liquid container.

In accordance with one illustrative embodiment of the invention, a wirelessly-enabled liquid container is provided that is dynamically configured to facilitate use-based messaging for a particular consumer of the liquid contents of the wirelessly-enabled liquid container. The wirelessly-enabled liquid container includes an upper portion including an opening and a liquid reservoir in communication with the opening; and a lower portion coupled to the upper portion. The lower portion includes at least one processor, a memory coupled to the processor, a transceiver coupled to the processor, at least one sensor unit coupled to the processor, and an audio unit coupled to the processor. The memory stores one or more audio messages. The sensor unit includes a first sensor that indicates when the wirelessly-enabled liquid container has moved so that the liquid contents of the wirelessly-enabled liquid container can be consumed. The audio unit includes a speaker that outputs the at least one or more audio messages under the control of the processor when the first sensor senses that the wirelessly-enabled liquid container has moved. The transceiver sends and receives data wirelessly. The data includes control information received from a remote device, and the processor is dynamically configured to select at least one of the one or more audio messages for playback via the speaker based on control information received from the remote device.

In accordance with another embodiment of the invention, a method is provided for implementing a wirelessly-enabled liquid container that is dynamically configured to facilitate use-based messaging for a particular consumer of the liquid contents of the wirelessly-enabled liquid container. The wirelessly-enabled liquid container includes an upper portion comprising an opening and a liquid reservoir in communication with the opening, and a lower portion coupled to the upper portion. The lower portion includes at least one processor, a memory coupled to the processor, a transceiver coupled to the processor, at least one sensor unit coupled to the processor, and an audio unit coupled to the processor. The memory stores one or more audio messages. The sensor unit includes a first sensor that indicates when the wirelessly-enabled liquid container has moved so that the liquid contents of the wirelessly-enabled liquid container can be consumed. The audio unit includes a speaker that outputs the at least one or more audio messages under the control of the processor when the first sensor senses that the wirelessly-enabled liquid container has moved. The transceiver sends and receives data wirelessly, the data including control information received from a remote device. The method includes receiving the control information from the remote device. The method also includes dynamically configuring the processor to select at least one of the one or more audio messages for playback via the speaker based on control information received from the remote device, sensing, via the first sensor, whether the wirelessly-enabled liquid container has moved, and outputting the at least one or more audio messages under the control of the processor when the first sensor senses that the wirelessly-enabled liquid container has moved.

In accordance with yet another illustrative embodiment, in a communication network having remote devices, including remote user device(s) and back end server device(s) communicating with at least one of the remote user device (s), and one or more wirelessly-enabled liquid containers, each of the wirelessly-enabled liquid containers includes an upper portion includes an opening and a liquid reservoir in communication with the opening, and a lower portion coupled to said upper portion. The lower portion includes at least one processor, a memory coupled to the processor, a transceiver coupled to the processor, at least one sensor unit coupled to the processor, and an audio unit coupled to the processor. The memory stores one or more audio messages. The sensor unit includes a first sensor that indicates when the wirelessly-enabled liquid container has moved so that the liquid contents of the wirelessly-enabled liquid container can be consumed. The audio unit includes a speaker that outputs the at least one or more audio messages under the control of the processor when the first sensor senses that the wirelessly-enabled liquid container has moved. The transceiver sends and receives data wirelessly, the data including control information received from at least one of the remote devices, and the processor is dynamically configured to select at least one of the one or more audio messages for playback via the speaker based on control information received from the at least one of the remote devices.

In accordance with yet another illustrative embodiment, a computer program product is provided including a non-transitory computer readable storage medium having computer readable program codes embodied therein. The computer readable program codes cause a processor within a wirelessly-enabled liquid container to receive control information from a remote device via a transceiver associated with the wirelessly-enabled liquid container; dynamically configure the processor to select one or more audio messages for playback via a speaker associated with the wirelessly-enabled liquid container based on control information received from the remote device, sense, via the first sensor, whether the wirelessly-enabled liquid container has moved; and output, via the speaker, the at least one or more audio messages under the control of the processor when the first sensor senses that the wirelessly-enabled liquid container has moved.

In accordance with the illustrative embodiments described above, the wirelessly-enabled liquid container may be a baby bottle, and the upper portion of the baby bottle may have a nipple coupled to an opening of the baby bottle.

In accordance with the illustrative embodiments described above, the sensor unit includes an accelerometer that detects motion of the wirelessly-enabled liquid container which may include the tilting of the wirelessly-enabled liquid container.

In accordance with the illustrative embodiments described above, the lower portion of the wirelessly-enabled liquid container includes a slot coupled to the processor that receives a memory card that stores at least one of the audio messages, and when a memory card is inserted into the slot it is coupled to said processor.

BRIEF DESCRIPTION OF THE DRAWINGS

In the following description, various embodiments of the present invention are described with reference to the following drawings, in which:

FIG. 2 is a depiction of portions of a system in which the wirelessly-enabled liquid container of FIGS. 1*a* and 1*b* may be deployed.

FIG. 3 is a flow chart describing the interaction of the wirelessly-enabled liquid container of FIGS. 1*a* and 1*b* and other components of the system of FIG. 2.

DETAILED DESCRIPTION OF THE EMBODIMENTS

Figure 1A:
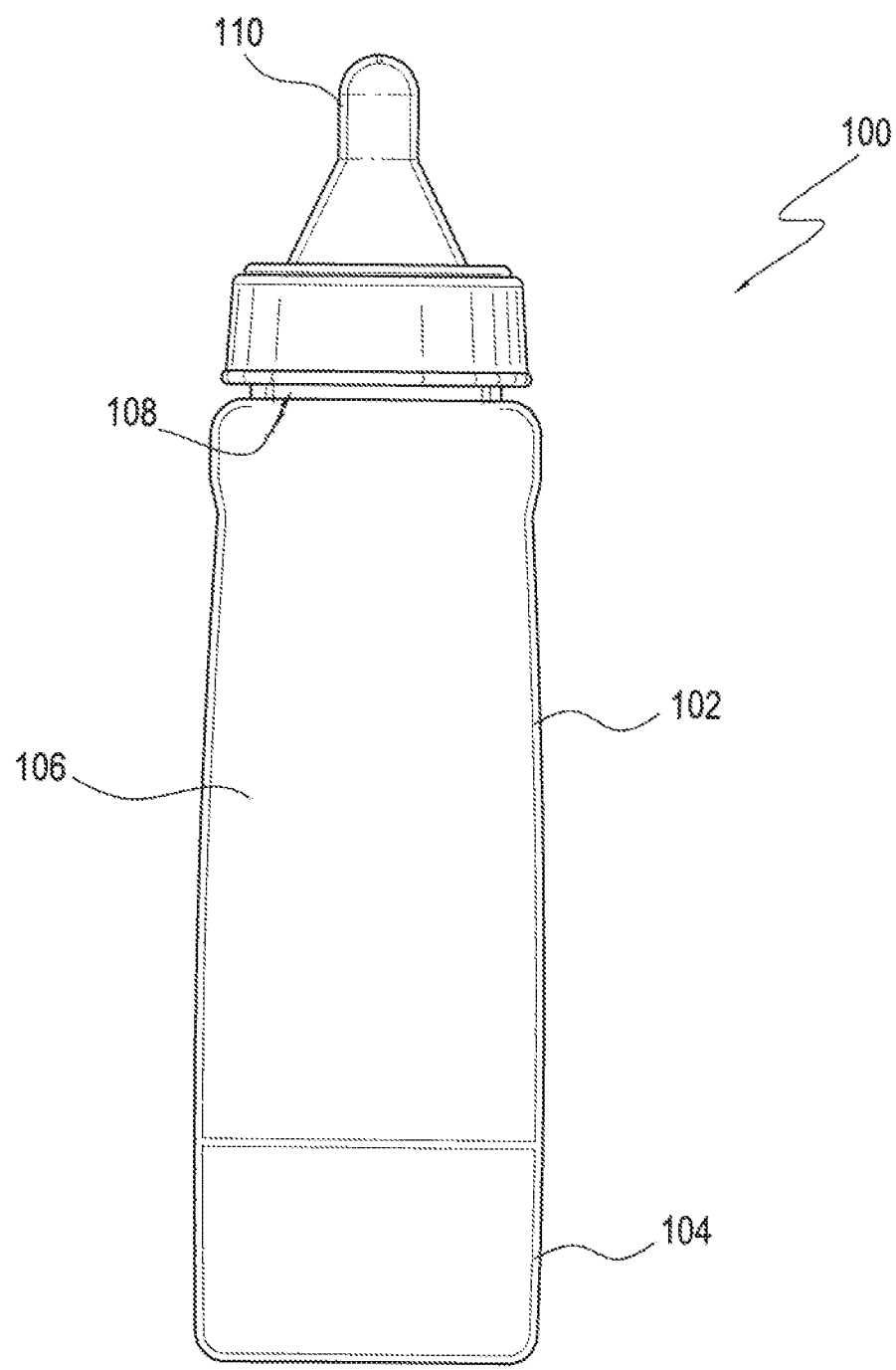
FIGS. 1*n* and 1*b* schematically depict an illustrative wirelessly-enabled liquid container in accordance with a preferred embodiment of the present invention.

In accordance with certain embodiments of the present invention, systems, apparatuses, computer readable media, and methods are disclosed for implementing a wirelessly-enabled liquid container including a processor that can be remotely and dynamically configured to change the liquid container's messaging capabilities for a particular consumer, such as a child in the case of a baby-bottle.

FIG. 1 schematically depicts a wirelessly-enabled liquid container 100 according to a preferred embodiment of the invention. The wirelessly-enabled liquid container 100 includes an upper portion 102 and a lower portion 104. According to one embodiment, the upper portion 102 includes a liquid reservoir 106 that includes an opening 108 through which a nipple 110 may extend. A lower portion of the nipple 110 is coupled to the reservoir 106 that contains a liquid. The upper and lower portions 102 and 104 can be a single unit or two separate pieces that are joined together by, for example, screwing the lower portion 104 into the upper portion 102. In that case, the lower rim of the upper portion 102 can be provided with screw threads. Similarly, the upper rim of the lower portion 104 can be provided with screw threads as well which accommodate the screw threads of the lower rim of the upper portion 102. Alternatively, instead of threads, the lower rim of the upper portion can have a small rubber ring affixed to its inner or outer surfaces. The rubber ring will retain the opposing inner or outer surface of the upper rim of the lower portion 104 so that the upper and lower portions 102 and 104 stay together until enough force is exerted in order to pull them apart.

The lower portion 104 of the liquid container 100 includes a control unit 200. The control unit 200 includes a processor 220 coupled to memory 224 including random access memory 226 and read only memory 227. In addition, the control unit 200 may include slot(s) 228 that receive memory card(s) 229, such as microSDHC Memory Card. The memory card may store message(s) downloaded from a network, or may more store pre-loaded messages.

Message(s), stored as the content(s) of audio file(s), may include educational messages (e.g., language instruction including English and foreign language, music appreciation, history, science, mathematical instruction, or other academic subjects), or advertising and other promotional messages (e.g., jingles).

The control unit 200 also include a communication module 230 coupled to the processor 220. The communications module 230 includes transceiver(s) 235, including a WiFi transceiver, a Bluetooth transceiver or some other wireless transceiver or combination of the foregoing transceivers. The communication module 230 also includes an antenna(s) 237 coupled to the transceiver(s) 235, which is coupled to the processor 220. The communication module 230 handles communications (via the transceiver(s) 235 and antenna(s) 237) with, for example, other components in the system described below in connection with FIG. 2. The lower portion 104 also includes a battery module 280, which may include one or more rechargeable or non-rechargeable batteries. The batteries may or may not be user replaceable.

The lower portion 104 also includes an audio unit 240 coupled to the processor 220. The audio unit 240 includes an analog to digital and digital to analog converter(s) 245 and transducers, such as a microphone 250 and speaker(s) 255. The lower portion 104 also includes a sensor unit 260 coupled to the processor 220 including one or more sensors. The sensors may include accelerometers, gravity sensors, gyroscopes that detect motion or rotation, such as the tilting, shaking, spinning or turning of the liquid container 100 in which it is incorporated. Additional sensors can include sound sensors to detect sound coming from the user of the liquid container 100 or touch sensors to detect the touch of a user of the liquid container 100. The speaker(s) 255 outputs the at least one or more audio messages under the control of the processor 220 when the first sensor senses that the wirelessly-enabled liquid container has moved.

The components of the control unit 200, the communications module 230 and the audio unit 240 can be incorporated into separate integrated circuit(s) or combined into a single integrated circuit, which may be an Application Specific Integrated Circuit (ASIC). In a preferred embodiment of the present invention, the lower portion 104 can have an upper wall 115 that extends across the lower portion 104 of the wireless-enabled liquid container 100. The upper wall 115 may contain compartment doors behind which slot(s) 228 and battery module 280 can be accessed. Thus, when the upper portion 102 is provided with screw threads and mated with the opposing screw threads on the outer rim of the lower portion 104, spilled liquid cannot reach the sensitive electronic components of the wireless-enabled liquid container 100. Also, a marine-grade speaker can be provided on, for example, a bottom surface of the lower portion 104 to ensure that liquid does not compromise the speaker or other internal components of the lower portion 104 of the wireless-enabled liquid container 100.

The lower portion 104 can be coupled to a separate base station 300 that includes a separate power adapter 310 for recharging any rechargeable batteries. The lower portion may include a mini USB connector to provide power via a USB cable attached to the base station 300.

Figure 1B:
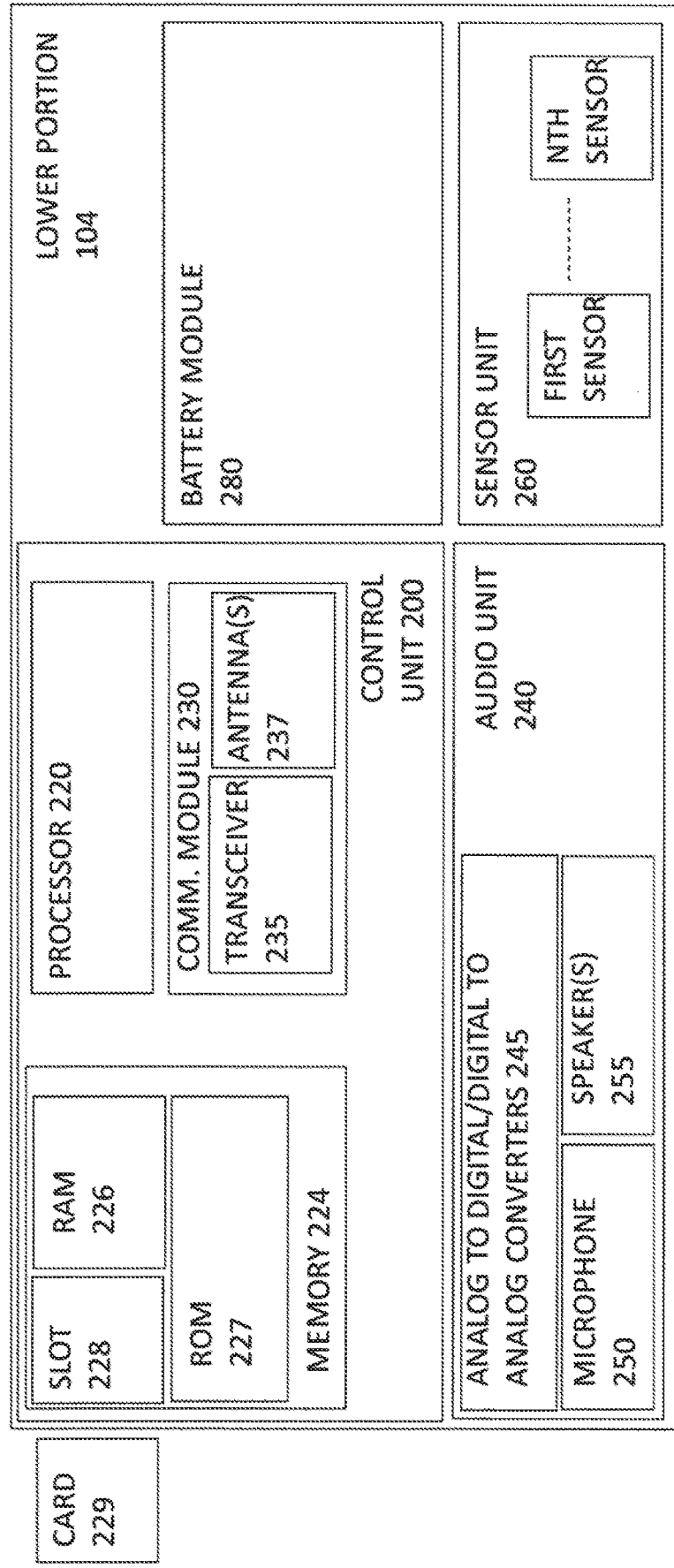

FIG. 2 depicts a system 400 incorporating wirelessly-enabled liquid containers 410, each of which may be a wirelessly-enabled liquid container 100 of the type shown in FIGS. 1a and 1b. The wirelessly-enabled liquid containers 410 communicate over a network 420 (such as the Internet) via, for example, a Hub 430 (e.g., wireless access point) with one or more remote device(s), including remote user device(s) 440 and remote back-end server device(s) 450. In addition, each of the remote user devices 440 may communicate with one or more of the remote back end server devices 450.

The remote user device(s) 440, such as a smartphone, tablet, or computer, each each incorporate a software application, which can communicate with one or more of the wirelessly-enabled liquid containers 410 to secure status information (e.g., error messages and/or current control information stored in memory 224 associated with the processor 220) related to the operation of the one or more wirelessly-enabled liquid containers 410 and to provide (updated) control information to the wirelessly enabled liquid containers 410 so that the processor(s) (e.g., 220) of one or more of the wirelessly-enabled liquid containers 410 can configure themselves to playback one of a number of particular messages via speaker(s) when sensor unit(s) (e.g. 260) indicates that one or more of the wirelessly-enabled liquid containers 410 have moved so that liquid may be consumed from the wirelessly-enabled liquid containers. The software application for the remote user devices can be downloaded from, for example, a web store, such as the Apple or Google web stores. By way of example, the processor (e.g., 220) can output a message via a digital to analog converter (e.g., 245) via an audio speaker situated in a lower portion of the one or more wirelessly-enabled liquid containers 410.

The control information provided by the remote devices (e.g., 440 and 450) to the wirelessly-enabled liquid containers 100 and 410 includes parameters such as the remote user device ID number, consumer ID, wirelessly-enabled liquid container IP address, wirelessly-enabled liquid container ID number, a message playlist ID number, message ID number, timer duration value, and sensor sensitivity value(s). The wirelessly-enabled liquid container IP address is an Internet Protocol ("IP") address associated with the wirelessly-enabled liquid container 100 and 410. The consumer ID reflects a number or other identifier associated with the person who will be consuming liquid from the wirelessly-enabled liquid container 100 and 410. The sensor sensitivity values can be LOW, MEDIUM, or HIGH depending on the sensor and the type of movement or other parameter (such as noise) that it senses. In the case of an accelerometer, a LOW sensitivity value means that the wirelessly-enabled liquid container must clear a higher threshold than for a MEDIUM or HIGH sensitivity value. As an example, a LOW sensitivity value may have 45 degree threshold, a MEDIUM sensitivity value may have a 30 degree threshold, and a HIGH sensitivity value may have a 15 degree threshold. This means that a wirelessly-enabled liquid container 100 and 410 with a LOW sensitivity setting must tilt more than 45 degrees before the processor will consider the wirelessly-enabled liquid container to have moved for the purposes of message playback. Similarly, a wirelessly-enabled liquid container 100 and 410 with a MEDIUM or HIGH sensitivity value must tilt more than 30 degrees or 15 degrees, respectively, before the processor will consider the wirelessly-enabled liquid container 100 and 410 to have moved for the purposes of message playback.

As an alternative implementation, no sensitivity value will be provided and the processor as configured will playback messages via the audio unit if the unit is moved. The processor will periodically check the output of the sensor(s) and will continue to playback messages if the sensor output(s) indicate that the wireless-enabled liquid container is moving. If the sensor output(s) indicates that it is not moving, then the processor will continue to playback messages for up to as long as the timer duration value (e.g., 15 minutes, 30 minutes, 45 minutes, 1 hour or two hours), specified in the control information, indicates that the playback of messages can continue after movement of the wirelessly-enabled liquid container 100 and 410 is no longer detected. The timer duration can also be set at a default value (e.g., 15 minutes, 30 minutes, 45 minutes, 1 hour or two hours. The processor 220 relies on a timer (implemented in software) to determine if the timer value output by the timer is within the period indicated by the timer duration value specified in the control information.

The remote back-end server device(s) 450 have an associated database 452 and may include software programs, including a wirelessly-enabled liquid container asset management application and a database application, that together manage messages, message playlists, and control information associated with a large number of wirelessly-enabled liquid devices and manage interactions with remote user devices. The aforementioned software programs may be distributed over multiple hardware devices.

In a preferred embodiment, the wirelessly-enabled liquid containers can be beverage containers and/or beverage container systems that are deployed in connection with a promotional campaign. By way of example, beer bottle containers or systems that are provided by Budweiser or Heineken can be delivered to sports stadiums with a predefined set of remote user device ID numbers and/or wirelessly-enabled liquid container ID numbers. Thereafter, a sports team or concert promoter, for example, may be provided with a remote user ID number and wirelessly-enabled liquid container ID number(s) within the pre-defined set, and could use the remote user device app to dynamically configure the processor within one of the wirelessly-enabled liquid container(s) corresponding to those wirelessly-enabled liquid container ID number(s) so that a particular message(s) (e.g., advertising or other promotional jingle(s)) can be played via the speaker(s) of those wirelessly-enabled liquid container(s) under the control of the processor(s) incorporated within the wirelessly-enabled liquid container(s).

In an alternative embodiment, the consumer of liquid from the beverage container may utilize a remote user device to remotely and dynamically configure the processor of a wirelessly-enabled liquid container to playback messages using a software application downloaded from an app store. Each consumer would be given a unique consumer ID when the software is registered to uniquely identify the consumer. The messages could include promotional messages related to upcoming events, such as a concert schedule or professional sports team schedule.

In those instances where it is preferable to not alter a beverage container to accommodate the electronics of the lower portion of the liquid container (shown in FIGS. 1a and 1b), a beverage container system can be provided that includes a beverage container (e.g., bottle or can) which is held within a beverage container holder, such as an insulated beverage container cooler. The lower portion of the beverage container holder can accommodate the components of the lower portion 104 shown in FIGS. 1a and 1b, without compromising the beverage container. Preferably, the insulated beverage container cooler is metallic (e.g., stainless steel), and doubled-walled so that the beverage container's liquid contents can remain cool for a prolonged period of time.

FIG. 3 is a flow chart describing the interaction of the wirelessly-enabled liquid container of FIGS. 1a and 1b and other components of the system of FIG. 2. The procedure 300 is illustrative, as procedures may contain more, fewer, and other steps than those depicted in FIG. 3.

In a first act 310, the wirelessly-enabled liquid container 100 and 410 receives the control information from the remote device. In a second act 320, the processor 220 is dynamically configured to select at least one of the one or more audio messages for playback via the speaker(s) 255 based on control information received from the remote device (e.g., 440 and 450). In a third act 330, the first sensor senses whether the wirelessly-enabled liquid container 100 and 410 has moved. In a fourth act 340, the speaker(s) 255 outputs one or more audio messages under the control of the processor when the first sensor of sensor unity 260 senses that the wirelessly-enabled liquid container has moved.

The procedure 300 is implemented, for example, by software running on the processor 220, which is stored in the memory 224 of the wirelessly-enabled liquid container 100 and 410. The processor 220 receives control information (e.g., parameters such as the remote user device ID number, consumer ID, wirelessly-enabled liquid container IP address, wirelessly-enabled liquid container ID number, a message playlist ID number, message ID number(s), timer duration value, and sensor sensitivity value(s)) from the remote device (e.g., 440 and 450) in act 310. In act 320, the processor 220 determines it current status which encompasses its current control information (e.g., parameters such as the remote user device ID number, consumer ID, wirelessly-enabled liquid container IP address, wirelessly-enabled liquid container ID number, a message playlist ID number, message ID number(s), timer duration value, and sensor sensitivity value(s)) and compares it control information (i.e., updated control information) received most recently from the remote device (e.g., 440 and 450) and updates the control information stored in the memory 224 associated with the processor 220. Thereafter, in step 330, the speaker(s) 255 outputs one or more audio messages (i.e., those messages having message ID numbers corresponding to the playlist ID number stored as the updated control information in memory 224) under the control of the processor 220 when the first sensor of the sensor unit 260 senses that the wirelessly-enabled liquid container has moved (in accordance with the sensitivity value(s) that are part of the updated control information).

If a sensitivity value has changed in the updated control information then there will be a difference in the degree to which the wirelessly-enabled liquid container must, for example, move before messages are played back via the speaker(s) 255 as compared to what occurred prior to the time the control information was last updated. Also, to the extent that the messages are different (i.e., have a different playlist ID number and message ID number), then those messages will be played after the next move is sensed in accordance with the sensitivity values found in the updated control information stored in memory 224.

Procedure 300 (as described above) is followed when the remote device is a remote user device 440. When the remote device is a remote back end server device 450, the remote user device communicates with the back-end server device 450 to provide control information to the back-end server device 450, which stores the control information in one or more database(s) 452 storing and managing control information associated with multiple remote user devices for many wirelessly-enabled liquid containers (e.g., 100 and 410). The remote user device 440 can provide message playlist(s) and message(s) directly to a wirelessly-enabled liquid container (e.g., 100 and 410) or it can rely on one or more remote back end server 450 devices to provide message playlist(s) and message(s) directly to the wirelessly-enabled liquid container (e.g., 100 and 410). Also, the remote user device 440 can provide control information directly to a wirelessly-enabled liquid container (e.g., 100 and 410) or it can rely on the remote back end server(s) to provide control information directly to the wirelessly-enabled liquid container (e.g., 100 and 410).

In an alternative embodiment, once the control information is updated by a remote device (e.g., 440 and 450) (having a remote user device ID number) for a particular wirelessly-enabled liquid container (e.g., 100 and 410) having a corresponding wirelessly-enabled liquid container ID number, the control information for all wirelessly-enabled liquid containers (e.g., 100 and 410) having wirelessly-enabled liquid container ID numbers associated with that remote user device ID number would be identically updated by the software on the remote device (e.g., 440 and 450).

Figure 4A:
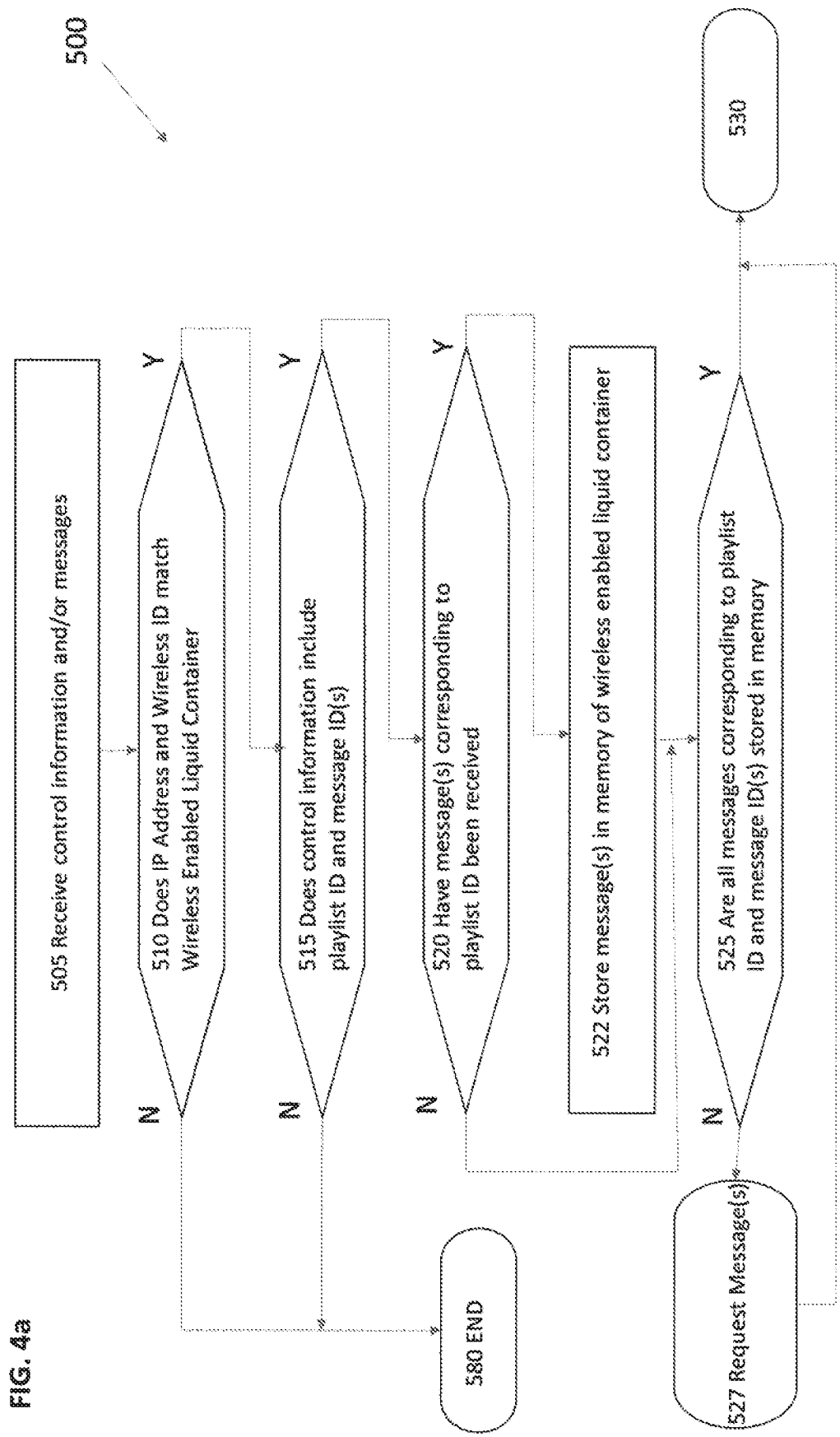
FIGS. 4*a* and 4*b* is a flow chart describing the configuration and operation of the wirelessly-enabled liquid container of FIGS. 1*a* and 1*b* and other components of, for example, the system of FIG. 2.
Figure 4B:
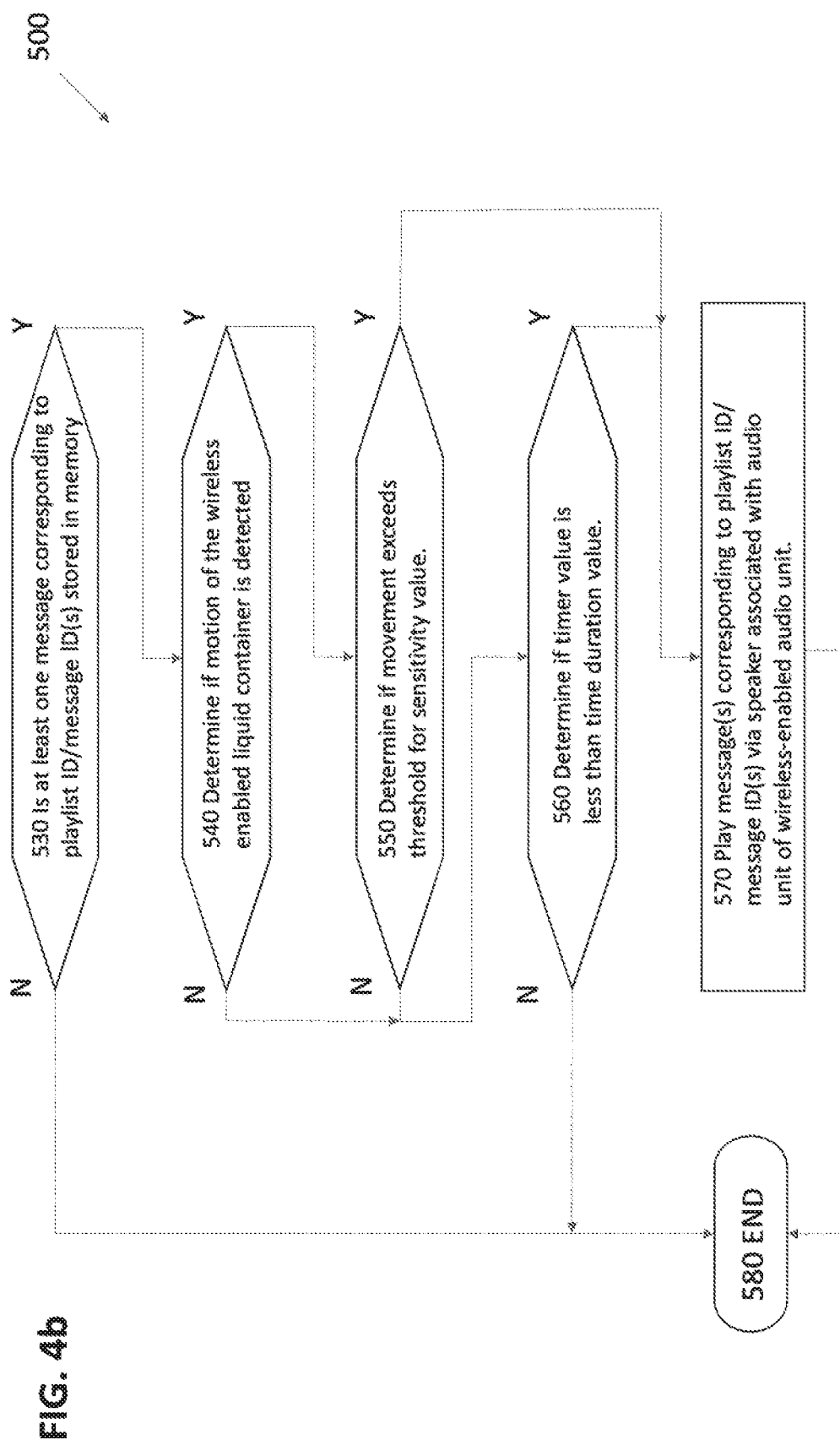

FIG. 4 is a flow chart depicting the configuration and operation of the illustrative wirelessly-enabled liquid container 100 and 410 of FIGS. 1a, 1b, and 2. The process 400 is illustrative, as procedures may contain more, fewer, and other steps than those depicted in FIG. 4.

In act 505 of the process 500, the wirelessly-enabled liquid container receives control information and/or messages. In act 510, software running on the processor 220 determines whether the IP address and wirelessly-enabled liquid container ID match the IP address and wirelessly-enabled liquid container ID stored in the memory 224 associated with the processor 220. In act 515, the software running on the processor 220 determines whether the received control information include a playlist ID and message ID(s) corresponding to the playlist ID. If so, in act 520, it is determined if any message(s) have been received along with the control information that correspond to the playlist ID. If so, in act 522, the processor stores the message(s) in memory 224 and/or memory card 229. If the answer to the determination in 520 is no, or the act 522 has completed, then in act 525, it is determined if all the messages (corresponding to the playlist ID and memory ID(s) received as control information) are stored in memory associated with the processor. If not, in act 527, the software on the processor requests messages over a network from a remote device via a communication module associated with the processor. If the answer is yes, in act 530, it is determined if there is at least one message (corresponding to the playlist ID and message ID(s) received in the control information) is stored in memory associated with the processor. If at least one message is stored in memory (corresponding to the playlist ID and message ID(s)), in act 540, it will be determined if motion of the wirelessly-enabled liquid container is detected. If so, in step 550, it is determined if the movement exceeds a threshold for the sensitivity value specified as part of the control information.

If the answer is no to the determinations that occur in acts 540 and 550, it will be determined in act 560, if the timer value is less than the timer duration value specified as part of the control information. If the answer is yes to the determinations that occur in acts 550 and 560, then in act 570, the software on the processor will play message(s) corresponding to playlist ID/message ID(s) specified as part of the control information via speaker(s) 255 associated with audio unit 240 of the wireless-enabled liquid container. If the answer to the determinations of acts 510, 515, 530, 560 is no, or the act 570 has completed, then the process 500 completes at 580, though the process is repeated periodically and/or when new control information and/or message(s) are received. Although the process 500 has been described in connection with software running on a processor, those skilled in the art would appreciate that it may be entirely implemented in hardware.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive. Moreover, the advantages of various embodiments of the invention are not limited to the advantages specifically described herein.

What is claimed is:

1. A wirelessly-enabled liquid container that is dynamically configured to facilitate use-based messaging for a particular consumer of the liquid contents of the wirelessly-enabled liquid container, the wirelessly-enabled liquid container comprising:
   an upper portion comprising an opening and a liquid reservoir in communication with the opening; and
   a lower portion coupled to said upper portion, said lower portion comprising at least one processor, a memory coupled to the processor, a transceiver coupled to the processor, at least one sensor unit coupled to the processor, and an audio unit coupled to the processor; wherein the memory stores one or more audio messages, wherein the sensor unit includes a first sensor that indicates when the wirelessly-enabled liquid container has moved so that the liquid contents of the wirelessly-enabled liquid container can be consumed, wherein the audio unit includes a speaker that outputs the at least one or more audio messages under the control of the processor when the first sensor senses that the wirelessly-enabled liquid container has moved, wherein the transceiver sends and receives data wirelessly, said data including control information provided by a remote device, said one or more messages being provided by at least one back end server separate from said remote device, and wherein the processor is dynamically configured to select at least one of the one or more audio messages for playback via the speaker based on control information provided by the remote device.

2. The wirelessly-enabled liquid container of claim 1, wherein the wirelessly-enabled liquid container comprises a sippy cup.

3. The wirelessly-enabled liquid container of claim 2, wherein the sippy cup is remotely and dynamically configured to provide use-based educational messaging for a child consumer of the liquid contents of the sippy cup.

4. The wirelessly-enabled liquid container of claim 1, wherein the sensor unit comprises an accelerometer that detects motion of the wirelessly-enabled liquid container.

5. The wirelessly-enabled liquid container of claim 4, wherein the accelerometer detects tilting of the wirelessly-enabled liquid container.

6. The wirelessly-enabled liquid container of claim 1, wherein the lower portion includes a slot coupled to said processor that receives a memory card that stores at least one of the audio messages.

7. The wirelessly-enabled liquid container of claim 6, wherein the memory card is inserted into the slot and is coupled to said processor.

8. The wirelessly-enabled liquid container of claim 1, wherein the one or more audio messages are provided by at least one back end server via a network, the at least one back end server including a wirelessly-enabled liquid container asset management application and a database application that together manage at least one of a message playlist and a plurality of audio messages including the one or more audio messages, control information associated with a plurality of wirelessly-enabled liquid container devices including the wirelessly-enabled liquid container, and interactions with a plurality of remote user devices including said remote device, wherein the one or more messages are provided by the at least one back end server, which is separate from said remote device, wherein control information includes a wirelessly-enabled liquid container ID number, at least one of a message playlist ID number and message ID number, a timer duration value, and at least one sensor sensitivity value, said speaker outputting the at least one or more audio messages for playback under the control of the processor based on the sensor sensitivity value and the timer duration value when the first sensor senses that the wirelessly-enabled liquid container has moved, wherein the at least one or more audio messages are selected based on the at least one of the message playlist ID number and message ID number, and wherein if the control information is updated such that the at least one of the message playlist ID number and message ID number is changed then a different one or more audio messages will be outputted by the audio unit under the control of the processor after a next move of the wirelessly-enabled liquid container is sensed in accordance with the sensor sensitivity value.

9. A method of implementing a wirelessly-enabled liquid container that is dynamically configured to facilitate use-based messaging for a particular consumer of the liquid contents of the wirelessly-enabled liquid container, the wirelessly-enabled liquid container including an upper portion comprising an opening and a liquid reservoir in communication with the opening, and a lower portion coupled to said upper portion, said lower portion comprising at least one processor, a memory coupled to the processor, a transceiver coupled to the processor, at least one sensor unit coupled to the processor, and an audio unit coupled to the processor; wherein the memory stores one or more audio messages, wherein the sensor unit includes a first sensor that indicates when the wirelessly-enabled liquid container has moved so that the liquid contents of the wirelessly-enabled liquid container can be consumed, wherein the audio unit includes a speaker that outputs the at least one or more audio messages under the control of the processor when the first sensor senses that the wirelessly-enabled liquid container has moved, wherein the transceiver sends and receives data wirelessly, said data including control information provided by a remote device, said one or more audio messages being provided by at least one back end server separate from said remote device; the method comprising:
- receiving the control information provided by the remote device;
- dynamically configuring the processor to select at least one of the one or more audio messages for playback via the speaker based on control information provided by the remote device;
- sensing, via the first sensor, whether the wirelessly-enabled liquid container has moved; and
- outputting the at least one or more audio messages provided by the at least one back end server under the control of the processor when the first sensor senses that the wirelessly-enabled liquid container has moved.

10. The method of claim 9, wherein the wirelessly-enabled liquid container comprises a sippy cup.

11. The method of claim 10, wherein the sippy cup is remotely and dynamically configured to provide use-based educational messaging for a child consumer of the liquid contents of the sippy cup.

12. The method of claim 9, wherein the sensor unit comprises an accelerometer that detects motion of the wirelessly-enabled liquid container.

13. The method of claim 12, wherein the accelerometer detects tilting of the wirelessly-enabled liquid container.

14. The method of claim 9, wherein the lower portion includes a slot coupled to said processor that receives a memory card that stores at least one of the audio messages.

15. The method of claim 14, wherein the memory card is inserted into the slot and is coupled to said processor.

16. In a communication network having remote devices, including remote user devices and at least one back end server device communicating with at least one of the remote user devices, and one or more wirelessly-enabled liquid containers, each of the wirelessly-enabled liquid containers comprising:
- an upper portion comprising an opening and a liquid reservoir in communication with the opening; and
- a lower portion coupled to said upper portion, said lower portion comprising at least one processor, a memory coupled to the processor, a transceiver coupled to the processor, at least one sensor unit coupled to the processor, and an audio unit coupled to the processor; wherein the memory stores one or more audio messages provided by the at least one back end server, wherein the sensor unit includes a first sensor that indicates when the wirelessly-enabled liquid container has moved so that the liquid contents of the wirelessly-enabled liquid container can be consumed, wherein the audio unit includes a speaker that outputs the at least one or more audio messages under the control of the processor when the first sensor senses that the wirelessly-enabled liquid container has moved, wherein the transceiver sends and receives data wirelessly, said data including control information received from at least one of the remote devices, and wherein the processor is dynamically configured to select at least one of the one or more audio messages for playback via the speaker based on control information received from the at least one of the remote devices.

17. In the communication network of claim 16, wherein the wirelessly-enabled liquid container comprises a sippy cup.

18. In the communication network of claim 17, wherein the sippy cup is remotely and dynamically configured to provide use-based educational messaging for a child consumer of the liquid contents of the sippy cup.

19. In the communication network of claim 16, wherein the sensor unit comprises an accelerometer that detects motion of the wirelessly-enabled liquid container.

20. In the communication network of claim 19, wherein the accelerometer detects tilting of the wirelessly-enabled liquid container.

21. In the communication network of claim 16, wherein the lower portion includes a slot coupled to said processor that receives a memory card that stores at least one of the audio messages, and wherein the memory card is inserted into the slot and is coupled to said processor.

22. A computer program product including a non-transitory computer readable storage medium having computer readable program codes embodied therein, the computer readable program codes causing a processor within a wirelessly-enabled liquid container to:
- receive control information from a remote device via a transceiver associated with the wirelessly-enabled liquid container;
- dynamically configure the processor to select one or more audio messages for playback via a speaker associated with the wirelessly-enabled liquid container based on control information received from the remote device, the one or more audio messages being received from at least one back end server;
- sense, via the first sensor, whether the wirelessly-enabled liquid container has moved; and
- output, via the speaker, the at least one or more audio messages under the control of the processor when the first sensor senses that the wirelessly-enabled liquid container has moved.

23. A wirelessly-enabled liquid container comprising:
- an upper portion comprising an opening and a liquid reservoir in communication with the opening; and
- a lower portion coupled to said upper portion, said lower portion comprising at least one processor, a memory coupled to the processor, a transceiver coupled to the processor, and at least one sensor unit coupled to the processor, wherein the memory stores one or more messages, wherein the sensor unit includes a first sensor that indicates when the wirelessly-enabled liquid container has moved, wherein the processor is configured to playback the at least one or more messages when the first sensor senses that the wirelessly-enabled liquid container has moved, wherein the transceiver sends and receives data wirelessly, said data including control information provided by a remote device, said one or more messages being provided by at least one back end server separate from said remote device, and wherein the processor is dynamically configured to select at least one of the one or more messages for playback based on control information provided by the remote device.

24. The wirelessly-enabled liquid container of claim 23, wherein the at least one or more messages comprise audio messages.

25. The wirelessly-enabled liquid container of claim 23, wherein the one or more messages are provided by at least one back end server via a network, the at least one back end server including a wirelessly-enabled liquid container asset management application and a database application that together manage at least one of a message playlist and a plurality of messages including the one or more messages, control information associated with a plurality of wirelessly-enabled liquid container devices including the wirelessly-enabled liquid container, and interactions with a plurality of remote user devices including said remote device, wherein the one or more messages are provided by the at least one back end server, which is separate from said remote device, wherein control information includes a wirelessly-enabled liquid container ID number, at least one of a message playlist ID number and message ID number, a timer duration value, and at least one sensor sensitivity value, said speaker outputting the at least one or more messages for playback under the control of the processor based on the sensor sensitivity value and the timer duration value when the first sensor senses that the wirelessly-enabled container has moved, wherein the at least one or more messages are selected for playback based on the at least one of the message playlist ID number and message ID number, and wherein if the control information is updated such that the at least one of the message playlist ID number and message ID number is changed then a different one or more messages will be played back under the control of the processor after a next move of the wirelessly-enabled liquid container is sensed in accordance with the sensor sensitivity value.

\* \* \* \* \*